(12) United States Patent
Terashima et al.

(10) Patent No.: US 6,616,822 B2
(45) Date of Patent: Sep. 9, 2003

(54) METHOD FOR PRODUCING A SILVER/SILVER HALIDE ELECTRODE AND ION-SELECTIVE ELECTRODE ELEMENT

(75) Inventors: Masaaki Terashima, Asaka (JP); Toshihisa Ito, Asaka (JP); Osamu Seshimoto, Asaka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/095,238

(22) Filed: Mar. 11, 2002

(65) Prior Publication Data

US 2002/0134679 A1 Sep. 26, 2002

Related U.S. Application Data

(62) Division of application No. 09/496,083, filed on Feb. 1, 2000, now abandoned.

(30) Foreign Application Priority Data

Feb. 1, 1999 (JP) ............................................. 11-024142
Feb. 1, 1999 (JP) ............................................. 11-024143

(51) Int. Cl.[7] ............................. G01N 27/30; B05D 5/12
(52) U.S. Cl. .................. 204/435; 427/126.1; 427/126.2
(58) Field of Search .......................... 204/435; 205/316, 205/507; 427/126.1, 126.2

(56) References Cited

U.S. PATENT DOCUMENTS

| | | | | |
|---|---|---|---|---|
| 1,602,595 A | * | 10/1926 | Sheppard et al. | |
| 3,354,069 A | * | 11/1967 | Jerrold-Jones et al. | |
| 3,806,439 A | * | 4/1974 | Light et al. | |
| 4,060,419 A | * | 11/1977 | Gerber et al. | |
| 4,116,798 A | * | 9/1978 | Magar et al. | |
| 4,214,968 A | * | 7/1980 | Battaglia et al. | |
| 4,259,164 A | * | 3/1981 | Rasch et al. | |
| 4,891,125 A | * | 1/1990 | Schultz | |
| 5,037,527 A | * | 8/1991 | Hayashi et al. | |

* cited by examiner

Primary Examiner—T. Tung
(74) Attorney, Agent, or Firm—Reed Smith LLP

(57) ABSTRACT

A silver/silver halide electrode composed of a non-electroconductive support sheet, a silver metal layer and a silver halide layer in order, is improved in its sensitivity by making the silver halide layer almost free from heavy metal element, for instance, by oxidizing the silver metal layer on its surface side with an oxidizing compound containing no heavy metal element or a chelated ferric oxidizing compound in the presence of a halide containing no heavy metal element.

6 Claims, 8 Drawing Sheets

$$\text{Log}\left[\frac{\text{Cl}^- \text{ Activity in Sample Solution}}{\text{Cl}^- \text{ Activity in Referential Solution}}\right]$$

METHOD FOR PRODUCING A SILVER/SILVER HALIDE ELECTRODE AND ION-SELECTIVE ELECTRODE ELEMENT

CROSS-REFERENCE TO RELATED APPLICATIONS

This application is a divisional application of U.S. application Ser. No. 09/496,083, filed on Feb. 1, 2000, now abandoned, which claims the priority of Japanese Patent Application Nos. 11-024142 and 11-024143, both of which were filed on Feb. 1, 1999.

FIELD OF THE INVENTION

This invention relates to a silver/silver halide electrode and further relates to an ion-selective silver/silver halide electrode element which is favorably employable for analysis of concentration of a biochemically active ion existing in body fluids such as blood, urine, and saliva.

BACKGROUND OF THE INVENTION

Various ions existing in body fluids, such as sodium ion, potassium ion, chloride ion, bromide ion, and iodide ion, can be quantitatively detected by means of an ion-selective silver/silver halide electrode element. Representative structure of the ion-selective silver/silver halide electrode element comprises, in order, a non-electroconductive support sheet, an electrode composite consisting essentially of a silver metal layer and a silver halide layer, an electrolytic material layer, and an ion-selective layer, the electrode composite being divided to give a pair of electrode units, and further comprising a referential liquid-receiving area and a sample liquid-receiving area each of which is provided on the ion-selective layer above each electrode unit, and an electroconductive bridge having two terminals, one terminal being placed in the referential liquid-receiving area and another terminal being placed in the sample liquid-receiving area.

The silver halide layer on the silver metal layer is generally produced by oxidizing the silver metal layer on its surface with an oxidizing compound in the presence of a halide containing a halide ion such as chloride ion.

Japanese Patent Provisional Publications No. 56-33537 and 56-33538 (corresponding to U.S. Ser. No. 66123 and No. 66124, respectively) describe the silver metal layer is oxidized using $KClCrO_3$, $K_3Fe(CN)_4$, $KMnO_4$, $K_2Cr_2O_7$, $NH_4VO_3$, $(NH_4)_2Ce(NO_3)_6$, or $Fe_2(C_2O_4)_3$, to prepare a silver/silver halide electrode.

SUMMARY OF THE INVENTION

As a result of studies performed by the present inventors, it has been discovered that an ion-selective silver/silver halide electrode element containing a silver halide layer which is produced by oxidizing the silver metal layer with a heavy metal element-containing oxidizing compound such as $KMnO_4$ or $K_2Cr_2O_7$, sometimes does not give a reliable analytical result.

Accordingly, it is an object of the present invention to provide an ion-selective silver/silver halide electrode element and a silver/silver halide electrode favorably employable for its manufacture.

The present invention resides in a silver/silver halide electrode comprising a non-electroconductive support sheet, a silver metal layer, and a silver halide layer, in order, wherein the silver halide layer contains essentially no heavy metal element.

The silver halide layer of the silver/silver halide electrode of the invention is preferably produced by oxidizing the silver metal layer on its surface side with an oxidizing compound containing no heavy metal element in the presence of a halide containing no heavy metal element.

The silver halide layer of the silver/silver halide electrode of the invention is also preferably produced by oxidizing the silver metal layer on its surface side with an oxidizing compound comprising a chelated ferric compound.

The invention further resides in an ion-selective silver/silver halide electrode element comprising, in order, a non-electroconductive support sheet, an electrode composite consisting essentially of a silver metal layer and a silver halide layer, an electrolytic material layer, and an ion-selective layer, the electrode composite being divided to give a pair of electrode units, and further comprising a referential liquid-receiving area and a sample liquid-receiving area each of which is provided on the ion-selective layer above each electrode unit, and a bridge having two terminals, one terminal being placed in the referential liquid-receiving area and another terminal being placed in the sample liquid-receiving area, wherein the silver halide layer contains no heavy metal element.

DETAILED DESCRIPTION OF THE INVENTION

Figure 1:
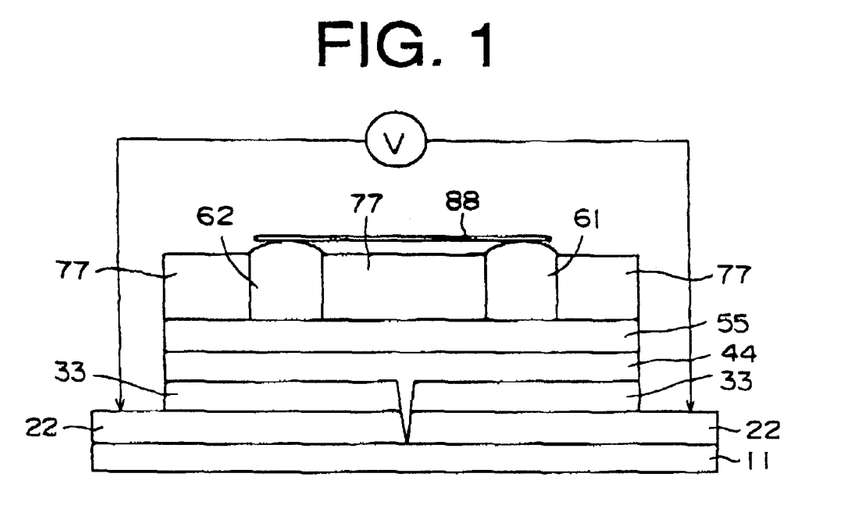
FIG. 1 schematically illustrates a structure of a representative ion-selective silver/silver halide electrode element of the invention.

A typical structure silver/silver halide electrode of the invention as well as a typical structure of the ion-selective silver/silver halide electrode element of the invention are illustrated in FIG. 1.

The ion-selective silver/silver halide electrode element of the present invention comprises, in order, a non-electroconductive support sheet 11, an electrode composite consisting essentially of a silver metal layer 22 and a silver halide layer 33, an electrolytic material layer 44 (the electrolytic material layer may be omitted in a chloride ion-selective electrode element), and an ion-selective layer 55. The electrode composite (which is composed of the silver metal layer 22 and silver halide layer 33) is divided to give a pair of electrode units. On the ion-selective layer 55, a sample liquid-receiving area 61 and a referential liquid-receiving area 62 are formed, each of which is provided above each of the divided electrode unit. Both area 61, 62 are surrounded by a mask 77 made of water-impermeable, non-electroconductive material. Between the sample liquid-receiving area 61 and the referential liquid-receiving area 62 are placed a bridge 88 having two terminals, in which one terminal is placed in the referential liquid-receiving area 62 and another terminal being placed in the sample liquid-receiving area 61, so that both area are electrically connected to each other when an aqueous electrolytic solution is placed on each of the liquid-receiving areas.

The non-electroconductive support sheet can be produced from glass, paper, or a resinous material such as polyethylene terephthalate, cellulose ester, polycarbonate of bisphenol A, polymethyl methacrylate, polyvinyl chloride, polypropylene, polystyrene, or polyvinyl alcohol. Polyethylene terephthalate and cellulose ester are preferably employed. Most preferred is polyethylene terephthalate.

The non-electroconductive support sheet preferably has a thickness of 50 μm to 1 mm, more preferably 80 to 400 μm.

On the non-electroconductive support sheet, the silver metal layer is formed. The formation of the silver metal layer can be made by any of known methods such as immersion coating, roll-coating, and brush-coating. The silver metal layer preferably has a thickness of 0.5 to 1 μm, more preferably 0.6 to 0.8 μm.

Each end area of the non-electroconductive support sheet should be covered with a hydrophobic polymer so that the silver layer under the covered area is not chlorinated. The covered area serves, after removal of the hydrophobic polymer, as an electroconductive terminal for applying to and detecting electric potential from the ion-selective electrode element.

The hydrophobic polymer for the coverage preferably comprises homopolymer or copolymer of vinyl chloride and/or vinylidene chloride. If a copolymer is employed, the copolymer preferably comprises a recurring unit derived from vinylidene chloride at least 50 mol. %, more preferably 80 mol. %. The comonomer (i.e., copolymerizable monomer) may be vinyl acetate, acrylic esters, methacrylic esters, maleic esters, acrylonitrile, ethylene, propylene, or vinyl ether. A vinyl chloride-vinylidene chloride copolymer can be preferably employed in various copolymerization ratios. It is more preferred for the copolymer to contain a recurring unit derived from vinylidene chloride in approximately 5 to 50 mol. %. The hydrophobic polymer preferably has a molecular weight of approx. 2,000 to 200,000, more preferably approx. 3,000 to 100,000.

The silver halide layer formed on the silver metal layer should not contain heavy metal elements such as Cr, Mn, and Fe. If the heavy metal elements are incorporated into the silver halide layer, their amounts should be as small as possible. For the reasons, the silver halide layer is formed on the silver metal layer by oxidizing, in the presence of a halide, the surface of the silver metal layer with an oxidizing compound containing no heavy metal elements or an oxidizing compound which is hardly incorporated into the silver halide metal layer or easily removed from the formed silver halide layer by washing or other methods.

The oxidation of the surface of the silver metal layer in the presence of a halide is preferably carried out by immersing the non-electroconductive support sheet having a silver metal layer on its surface in an aqueous solution containing an oxidizing compound and a halide. The support sheet having a silver metal layer whose surface layer has been converted into a silver halide layer is then washed with water and dried. A series of these steps, namely, halogenation, washing and drying, can be performed continuously in an automated machine.

The oxidizing compound preferably contains no heavy metal element, and hence hydrogen peroxide is favorably employed. Hydrogen peroxide is preferably employed in aqueous 1 to 10 vol. % solution. Hydrogen peroxide produces bubbles in the oxidizing reaction, which are advantageous for performing uniform reaction. Moreover, since hydrogen peroxide decomposes in the reaction to produce gaseous oxygen and water, which are not kept in the resulting silver halide layer. Other heavy metal element free oxidizing agents such as potassium peroxodisulfate ($K_2S_2O_8$) and Sodium peroxodisulfate ($Na_2S_2O_8$) are also employable for the formation of a silver halide layer on the silver metal layer.

In place of the heavy metal element free oxidizing compound, a chelated ferric compound can be employed. The chelated ferric compound serves for oxidizing the surface layer of the silver metal layer and hardly remains in the resulting silver halide layer after the silver halide layer is washed with water after the oxidation reaction. The chelated ferric compound for the oxidation is preferably used in an aqueous solution containing 100 to 500 mM, more preferably 150 to 250 mM, of the chelated ferric compound.

The chelating compound preferably is an aminocarboxylic acid or its derivative. Examples of the aminocarboxylic acids and their derivatives include propanediamine tetraacetate (PDTA), ethylenediamine tetraacetate (EDTA), diethylenetriamine pentaacetate (DTPA), triethylenetetramine hexaacetate (THHA), ethylenediamine disuccinate (EDDS), and tetrasodium N,N-dicarboxymethylglutamate (GLDA.4Na). Propanediamine tetraacetate (PDTA) and ethylenediamine tetraacetate (EDTA) are preferred. Accordingly, the chelated ferric compound preferably is PDTA.$Fe^{3+}$ or EDTA.$Fe^{3+}$. Most preferred is PDTA.$Fe^{3+}$.

The chelated ferric compound turns into a chelated ferrous compound after it oxidizes the silver metal. The chelated ferrous compound can be converted into the chelated ferric compound by oxidizing it with hydrogen peroxide or other oxidizing agent. Accordingly, the chelated ferric compound can be used repeatedly.

The halide employed in combination with the oxidizing compound preferably is a heavy metal free halide such as sodium halide. If the silver halide layer is a silver chloride layer, the halide preferably is sodium chloride. The halide is preferably used in an aqueous solution containing 50 to 150 mM of the halide.

The silver halide layer preferably has a thickness of approx. 1/3 to 1/2 of the silver metal layer.

On the silver halide layer is provided an electrolytic material layer. The electrolytic material layer can be provided on the silver halide layer by, for instance, coating an aqueous solution of the electrolytic material. The electrolytic material may be a halide of ammonium, an alkali metal, an alkaline earth metal, or one of their mixtures. For instance, if the silver halide layer is a silver chloride layer, the electrolytic material preferably is sodium chloride. If a potassium ion should be detected by the ion-selective electrode element, the electrolytic material may be sodium chloride or potassium chloride. In this case, potassium chloride is preferably used. If the ion-selective electrode element is prepared for the detection of chloride ion, the electrolytic material layer may be omitted. The electrolytic material layer can be coated on the silver halide layer in an amount of 1 to 10 g/m$^2$.

On the electrolytic material layer (or membrane) is provided an ion-selective layer. The ion-selective layer can be a solid layer or a solution layer. The solid layer can be a glass layer, a single crystal layer, or a sparingly soluble precipitate layer. The solution layer can be a liquid ion-exchange layer or a neutral carrier layer. The sparingly soluble precipitate layer is produced by molding under pressure a precipitate, optionally in combination with silicon rubber matrix, to give a pellet. The liquid layer may be formed of a non-aqueous solution of ion-exchange material or neutral carrier. The liquid layer can be supported by a polymer membrane such as polyvinyl chloride membrane. The ion-selective layer is preferably formed on the electroconductive material layer by roll coating, using an appropriate ion-selective material. The ion-selective material layer preferably has a thickness of 5 to 50 $\mu$m.

On the ion-selective layer, a water-impermeable mask of non-electroconductive material is formed. The mask should have two openings, one of which is for placing a sample solution in it, and another of which is for placing a referential solution in it. The openings are electrically connected by an electroconductive bridge, so that the sample solution and the referential solution placed on the openings are electrically connected. The mask can be fixed on the ion-selective layer using an adhesive (e.g., pressure-sensitive adhesive or hot-melt adhesive), fusion, or mechanical connecting means.

The openings may have a diameter of 2 to 5 mm, so that a sample solution or a referential solution of 5 to 5 $\mu$L volume can be spotted in the openings.

The electroconductive bridge can be made of fibrous porous material which can keep an aqueous electrolytic solution in its structure. The fibrous material can be twinned polyethylene fiber. The bridge can be prepared from membrane filter, paper filter, paper filter having a hydrophobic polymer layer on both surfaces.

The sample solution can be any of aqueous solutions such as blood, serum, plasma, urine, saliva, other body fluids, or other aqueous solutions collected from tap water, river, drainage, or industrial aqueous waste.

The measurement of ionic activity can be performed by a known method. In the measurement, the ionic activity is determined from the difference between the electric potential produced in the sample solution side (E-sample) and the electric potential produced in the referential solution side (E-reference) by the following equation:

$$E\text{-sample} - E\text{-reference} = (N/z) \times \log (\text{activity of sample solution/activity of referential solution}).$$

In the equation, N is a Nernst's constant (which is 59.2 mV at 25° C.) and z is an ionic equivalent.

The present invention is further described by the following examples.

EXAMPLE 1

(1) Preparation of Support Sheet having Silver Metal Layer

On a longitudinal polyethylene terephthalate film (length: approx. 150 m, width: 45 mm) was vacuum deposited silver metal to form a silver metal layer of 0.8 $\mu$m thick. The silver metal layer was divided into two parts which were electrically insulated. The silver metal deposited film was cut in the width direction to give a specimen having a width of 24 mm.

(2) Coverage of the Silver Metal Layer on Both End Areas

The silver metal layer on the support sheet was covered on its both end portions (5 mm length) with an oil soluble polymer (Flonmask MA-1, available from Furufuji Industries, Co., Ltd.) and the coated layer was dried.

(3) Preparation of Silver Metal/Silver Halide Electrode

In a measuring cylinder were placed 30 vol. % aqueous hydrogen peroxide, sodium chloride (100 mM) and purified water to give an aqueous solution of 5 vol % hydrogen peroxide. The resulting aqueous solution was made to pH 4.6 using 0.1 N hydrochloric acid, and then placed in a reaction vessel. The support sheet having the both end covered-silver metal layer was placed in the reaction vessel and immersed in the solution at room temperature (approx. 25° C.) for 3 min. Thus treated support sheet was taken out, washed with water and dried to 50° C., to give a silver metal/silver halide electrode.

(4) Preparation of Ion-selective Electrode Element

On the silver metal/silver halide electrode was coated an aqueous sodium chloride solution to form an electrolytic material layer. On the electrolytic material layer was coated an ethanolic solution of tri-n-octyl-methylammonium chloride and polyvinyl butyral, to give a chloride ion-selective layer. On the ion-selective layer was placed a dual adhesive tape having two openings in such manner that each opening was positioned above each of the divided silver metal layer. Subsequently, a fiber thread bridge was placed to connect the two openings, to prepare a chloride ion-selective electrode element of the invention having a structure illustrated in FIG. 1.

In the same manner, a potassium ion-selective electrode element and a sodium ion-selective electrode element according to the invention were prepared using an aqueous potassium chloride solution and an aqueous sodium solution, respectively.

EXAMPLE 2

(1) Measurement of Electric Potential in the use of Chloride Ion-selective Electrode Element 1) The following electrolyte-containing standard solutions L, M, and H were prepared.

TABLE 1

|  | Standard Solution | | |
| --- | --- | --- | --- |
|  | L | M | H |
| Sodium chloride | 70 mM | 100 mM | 140 mM |
| Sodium hydrogen-carbonate | 20 mM | 30 mM | 30 mM |
| Potassium dihydrogen phosphate | 2.5 mM | 4 mM | 6 mM |
| PVPK(polyvinyl pyrrolidone)-15 | 3 vol. % | 3 vol. % | 3 vol. % |
| Glycerol | 2 vol. % | 2 vol. % | 2 vol. % |

2) The standard solution L (sample solution) and the standard solution M (referential solution) were simultaneously spotted on the sample solution-receiving area and the referential solution-receiving area of the chloride ion-selective electrode element prepared in Example 1. At 60 min. after the spotting, an electric potential was measured using a potentiometer (Type 901, available from Orion Co., Ltd.). The same measurement of potential was performed replacing the standard solution L with the standard solutions M and H.

Figure 2:
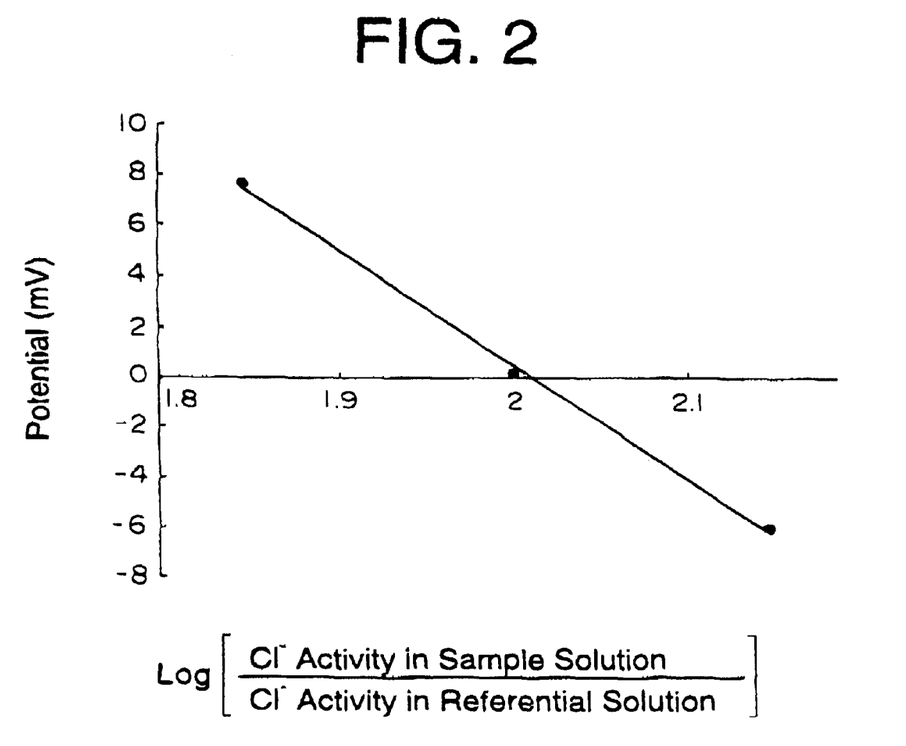
FIG. 2 graphically illustrates the relationship between an electric potential with a logarithmic number of a ratio of an ionic activity of a standard liquid L against an ionic activity of a referential liquid (i.e., standard liquid M) [Log (ionic activity of Liquid L/ionic activity of Liquid M)] which was observed in the use of a chlorine ion-selective electrode element of Example 2.

The results are illustrated in FIG. 2. In FIG. 2, the electric potential is plotted with respect to Log [(chloride ion activity in sample solution)/(chloride ion activity in referential solution)].

In FIG. 2, the left point was an electric potential measured using Standard Solution L as sample solution, the center point was an electric potential measured using Standard Solution M as sample solution, and the right point was an electric potential measured using Standard Solution H.

The straight line connecting these points of FIG. 2 is expressed by the following equation:

$$Y = -45.649X + 91.754$$

wherein X is a value of Log [(chloride ion activity in sample solution)/(chloride ion activity in referential solution)], and Y is an electric potential.

From the linear response illustrated in FIG. 2, it is confirmed that the chloride ion-selective electrode element of the invention shows a proper response according to Nernst' equation.

3) On the chloride ion-selective electrode element were spotted Standard Solution L (sample solution) and Standard Solution M (referential solution) simultaneously. Subsequently, an electric potential was measured every 6 seconds. The measurement was made three or four times. The same measurement was repeated using Standard Solutions M and H as sample solutions in placed of Standard Solution L.

Figure 3:
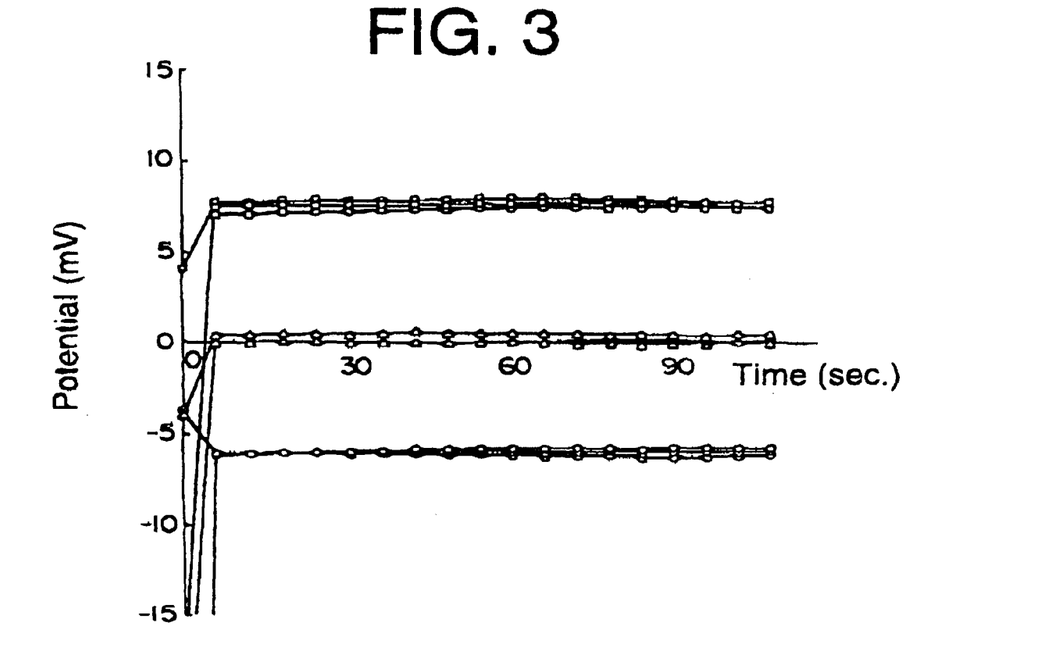
FIG. 3 graphically illustrates analytical performances of the chloride ion-detective electrode element of Example 2.

The results of measurements were graphically illustrated in FIG. 3, wherein the blank squares indicate the data measured using Standard Solution L as sample solution, the blank triangles indicate the data measured using Standard Solution M as sample solution, and the blank circles indicate the data measured using Standard Solution H as sample solution.

The results illustrated in FIG. 3 teach that a response in the measurement is quick and the measured value rapidly converges.

(2) Measurement of Electric Potential in the use of Potassium Ion-selective Electrode Element The measuring procedures of electric potential were repeated in the same manner as described above, for measuring potassium ion, using Standard Solutions L, M, and H, except for using the potassium ion-selective electrode element (which was prepared in Example 1) in place of the chloride ion-selective electrode element.

Figure 4:
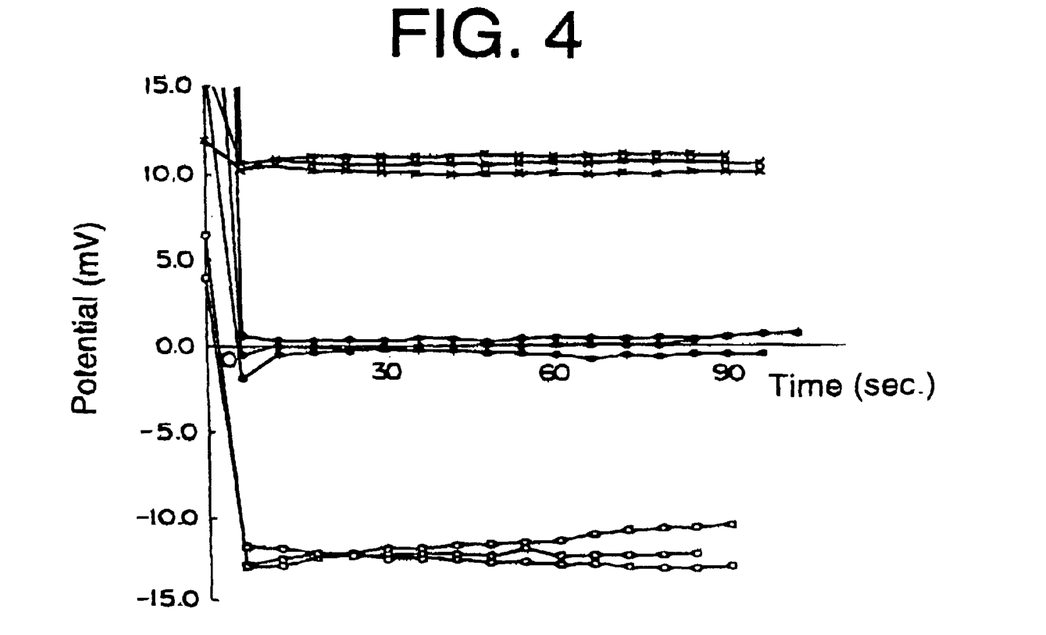
FIG. 4 graphically illustrates analytical performances of the potassium ion-detective electrode element of Example 2.

The results of the measurements are illustrated in FIG. 4, in the same manner as in FIG. 3. It is confirmed that a response in the measurement of potassium ion according to Nernst' equation is quick and the measured value rapidly converges.

(3) Measurement of Electric Potential in the use of Sodium Ion-selective Electrode Element The measuring procedures of electric potential were repeated in the same manner as described above, for measuring sodium ion, using Standard Solutions L, M, and H, except for using the sodium ion-selective electrode element (which was prepared in Example 1) in place of the chloride ion-selective electrode element.

Figure 5:
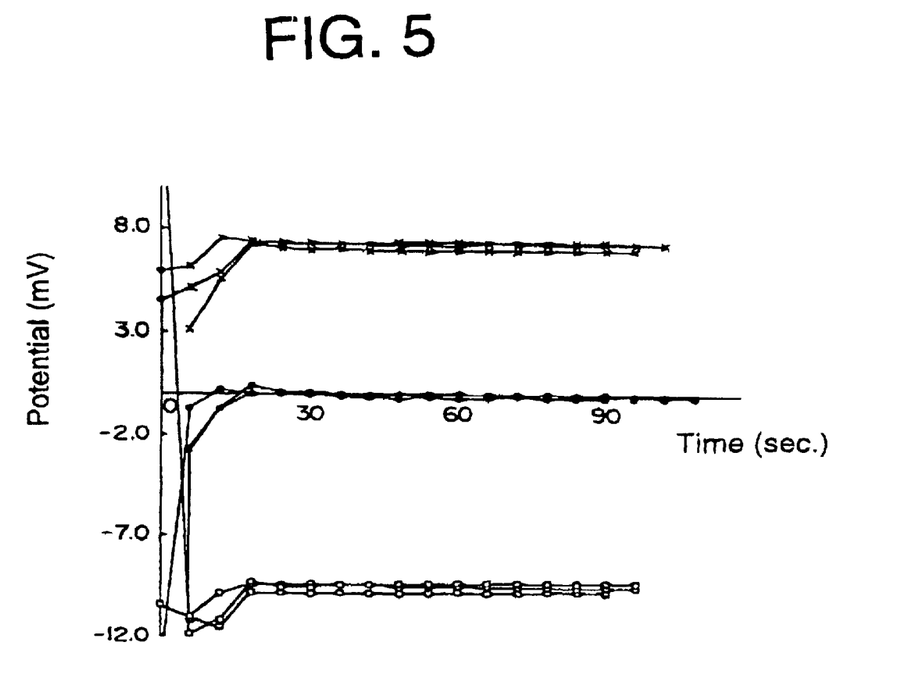
FIG. 5 graphically illustrates analytical performances of the sodium ion-detective electrode element of Example 2.

The results of the measurements are illustrated in FIG. 5, in the same manner as in FIG. 3. It is confirmed that a response in the measurement of sodium ion according to Nernst' equation is quick and the measured value rapidly converges.

Comparison Example 1

The silver/silver halide electrodes were prepared in the same manner as in Example 1, except for using potassium dichromate as the oxidizing compound in place of hydrogen peroxide. Oxidation was performed at 25° C. for 90 sec.

The procedures for preparing an ion-selective electrode element of Example 1 were repeated using the above-mentioned silver/silver halide electrodes, to give a chloride ion-selective electrode element, a potassium ion-selective electrode element, and a sodium ion-selective electrode element.

The measurement of electric potential described in Example 2 was repeated using the above-obtained three kinds of the ion-selective electrode elements. The results are graphically illustrated in FIG. 6 (for the chloride ion-selective electrode element), FIG. 7 (for the potassium ion-selective electrode element), and FIG. 8 (for the sodium ion-selective electrode element).

Figure 6:
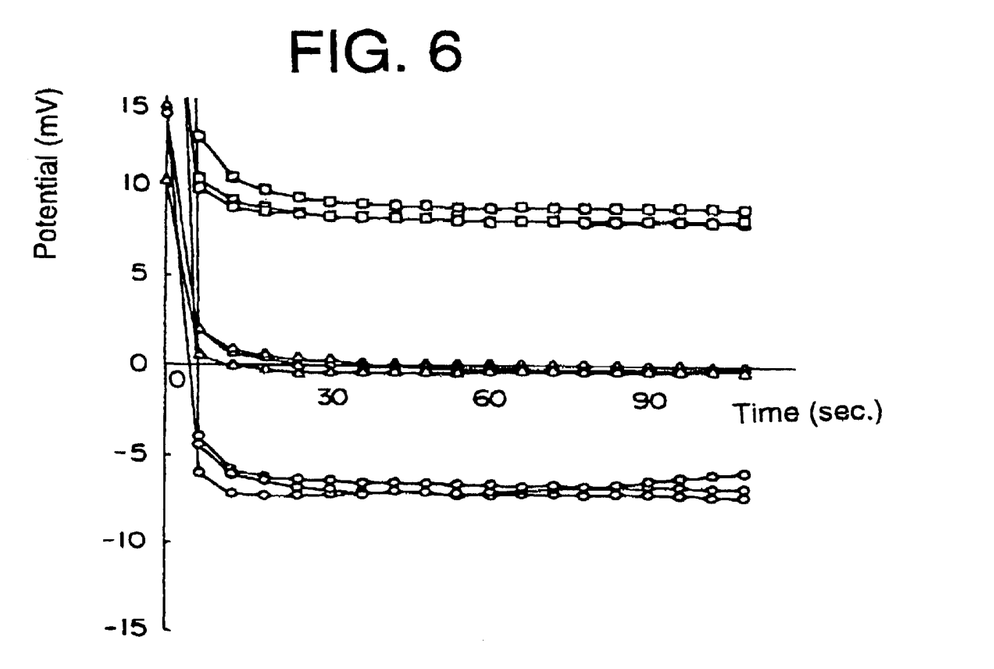
FIG. 6 graphically illustrates analytical performances of the chloride ion-detective electrode element of Comparison Example 1.
Figure 7:
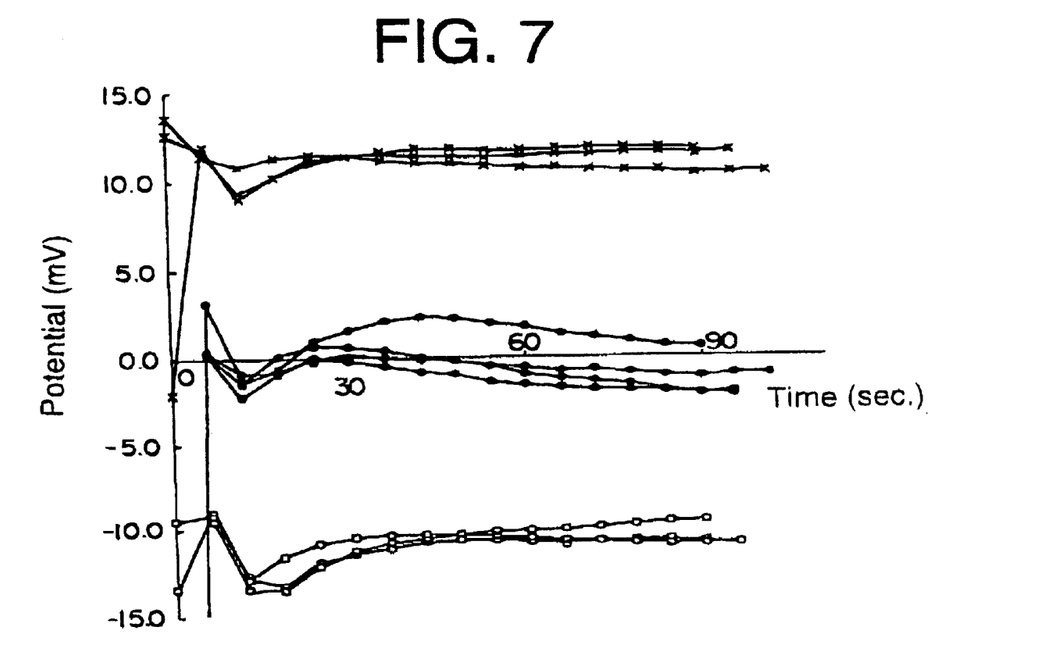
FIG. 7 graphically illustrates analytical performances of the potassium ion-detective electrode element of Comparison Example 1.
Figure 8:
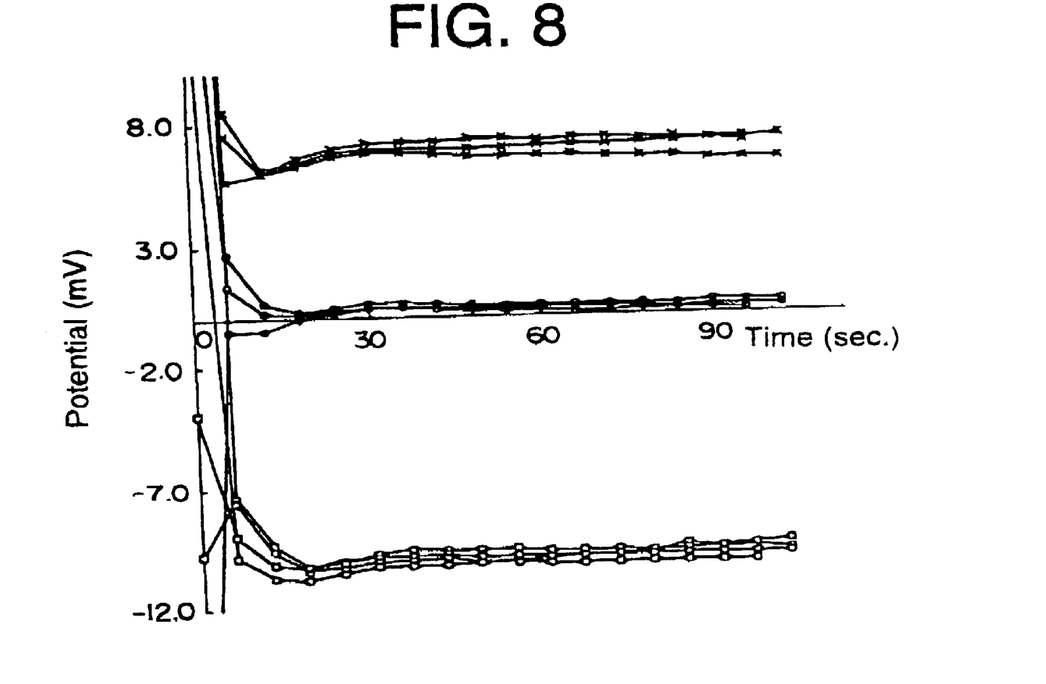
FIG. 8 graphically illustrates analytical performances of the sodium ion-detective electrode element of Comparison Example 1.

In FIG. 6, the blank squares, triangles and circles have the same meanings as in FIG. 3. In FIG. 7 and FIG. 8, cross marks, black circles and blank squares indiate, respectively, the measured values in the use of Standard Solutions L, M and H as the sample solutions.

In the results shown in FIGS. 6, 7 and 8, it is noted that the ion-selective electrode elements whose silver halide layer is prepared using potassium dichromate as the oxidizing compound are slow in their response and their convergences are low. Particularly, the potassium ion-selective electrode element shows poor convergence in the potential measurement.

Comparison Example 2

The silver/silver halide electrodes were prepared in the same manner as in Example 1, except for using potassium permanganate as the oxidizing compound in place of hydrogen peroxide.

The procedures for preparing a chloride ion-selective electrode element of Example 1 were repeated using the above-mentioned silver/silver halide electrodes.

The measurement of electric potential described in Example 2 was repeated using the above-obtained chloride ion-selective electrode element. The results are graphically illustrated in FIG. 9.

Figure 9:
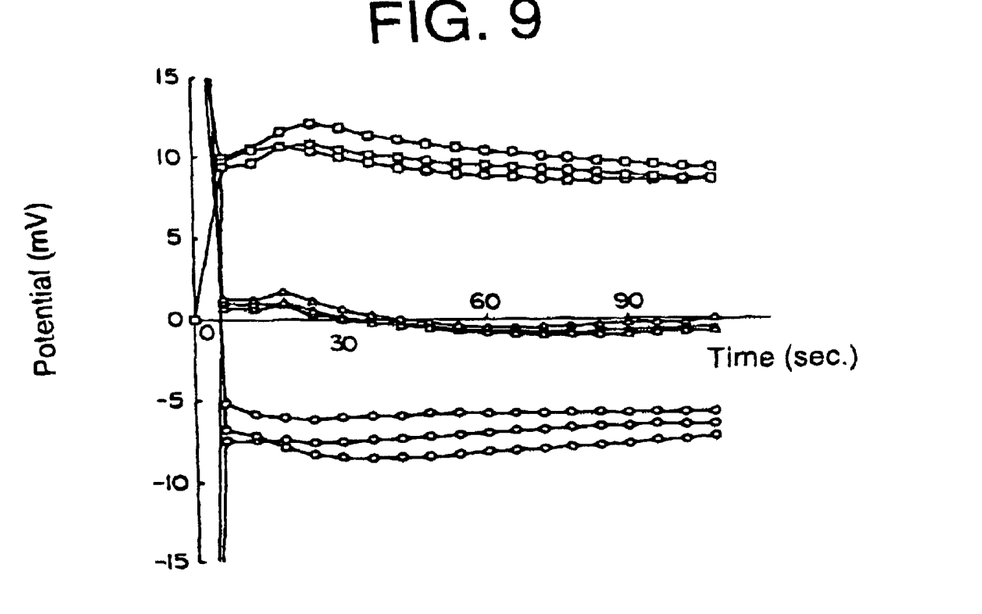
FIG. 9 graphically illustrates analytical performances of the chloride ion-detective electrode element of Comparison Example 2.

In FIG. 9, the blank squares, triangles and circles have the same meanings as in FIG. 3.

In the results illustrated in FIG. 9, it is noted that the chloride ion-selective electrode element whose silver halide layer is prepared using potassium permanganate as the oxidizing compound is poor in its convergence of response.

EXAMPLE 3

The elemental analyses were performed on the silver/silver halide electrode prepared in Example 1, Comparison Example 1, and Comparison Example 2, by means of a fluorescence X-ray meter (SEA 2001, available from Seiko Electronics Industry Co., Ltd.), to determine the amounts of several elements in the electrode. The results are set forth in Table 2, wherein the values are indicated in terms of strength (cps) of fluorescence X-rays.

TABLE 2

| | Silver/Silver Halide Electrode | | |
|---|---|---|---|
| | Example 1 | Com. Ex. 1 | Com. Ex. 2 |
| Chlorine | 129.75 | 140.93 | 121.33 |
| Chromium | 0.00 | 75.36 | 0.00 |
| Manganese | 0.00 | 0.00 | 52.09 |
| Silver | 280.55 | 288.94 | 291.28 |

It is confirmed that the silver/silver halide electrode prepared in Comparison Examples 1 and 2 are stained with heavy metals such as Cr and Mn.

EXAMPLE 4

(1) Preparation of Support Sheet having Silver Metal Layer

On a longitudinal polyethylene terephthalate film (length: approx. 150 m, width: 45 mm) was vacuum deposited silver metal to form a silver metal layer of 0.8 μm thick. The silver metal layer was divided into two parts which were electrically insulated. The silver metal deposited film was cut in the width direction to give a specimen having a width of 24 mm.

(2) Coverage of the Silver Metal Layer on Both End Areas

The silver metal layer on the support sheet was covered on its both end portions (5 mm length) with an oil soluble polymer (Flonmask MA-1, available from Furufuji Industries, Co., Ltd.) and the coated layer was dried.

(3) Preparation of Silver Metal/Silver Halide Electrode

In a reaction vessel was placed 500 mL of an aqueous solution (pH 4.6) containing 200 mM of Fe(III)-PDTA (ferric propanediamine tetracarboxylate), 50 mM of acetic acid, 50 mM of sodium acetate, and 100 mM of sodium chloride. The support sheet having the both end covered-silver metal layer was placed in the reaction vessel and immersed in the solution at room temperature (approx. 25° C.) for 180 seconds. Thus treated support sheet was taken out, washed with water and dried to 50° C., to give a silver metal/silver halide electrode.

(4) Preparation of Ion-selective Electrode Element

On the silver metal/silver halide electrode was coated an aqueous sodium chloride solution to form an electrolytic material layer. On the electrolytic material layer was coated an ethanolic solution of tri-n-octyl-methylammonium chloride and polyvinyl butyral, to give a chloride ion-selective layer. On the ion-selective layer was placed a dual adhesive tape having two openings in such manner that each opening was positioned above each of the divided silver metal layer. Subsequently, a fiber thread bridge was placed to connect the two openings, to prepare a chloride ion-selective electrode element of the invention having a structure illustrated in FIG. 1.

In the same manner, a potassium ion-selective electrode element and a sodium ion-selective electrode element according to the invention were prepared using an aqueous potassium chloride solution and an aqueous sodium solution, respectively.

EXAMPLE 5

(1) Measurement of Electric Potential in the use of Chloride Ion-selective Electrode Element 1) The standard solutions L, M and H were prepared in the same manner as in Example 2.

2) The standard solution L (sample solution) and the standard solution M (referential solution) were simultaneously spotted on the sample solution-receiving area and the referential solution-receiving area of the chloride ion-selective electrode element prepared in Example 1. At 60 min. after the spotting, an electric potential was measured using a potentiometer (Type 901, available from Orion Co., Ltd.). The same measurement of potential was performed replacing the standard solution L with the standard solutions M and H.

Figure 10:
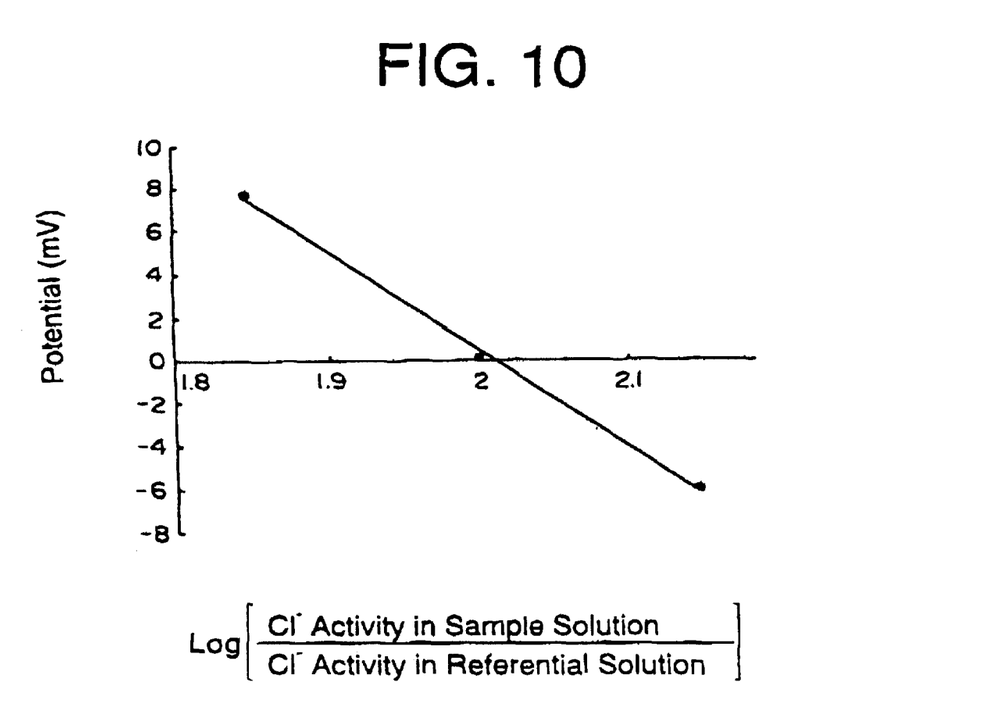
FIG. 10 graphically illustrates the relationship between an electric potential with a logarithmic number of a ratio of an ionic activity of a standard liquid L against an ionic activity of a referential liquid (i.e., standard liquid M) [Log (ionic activity of Liquid L/ionic activity of Liquid M)] which was observed in the use of a chlorine ion-selective electrode element of Example 5.

The results are illustrated in FIG. 10. In FIG. 10, the electric potential is plotted with respect to Log [(chloride ion activity in sample solution)/(chloride ion activity in referential solution)].

In FIG. 10, the left point was an electric potential measured using Standard Solution L as sample solution, the center point was an electric potential measured using Standard Solution M as sample solution, and the right point was an electric potential measured using Standard Solution H.

The straight line connecting these points of FIG. 10 is expressed by the following equation:

$$Y = -47.414X + 95.145$$

wherein X is a value of Log [(chloride ion activity in sample solution)/(chloride ion activity in referential solution)], and Y is an electric potential.

From the linear response illustrated in FIG. 10, it is confirmed that the chloride ion-selective electrode element of the invention shows a proper response according to Nernst' equation.

3) On the chloride ion-selective electrode element were spotted Standard Solution L (sample solution) and Standard Solution M (referential solution) simultaneously. Subsequently, an electric potential was measured every 6 seconds. The measurement was made three or four times. The same measurement was repeated using Standard Solutions M and H as sample solutions in placed of Standard Solution L.

Figure 11:
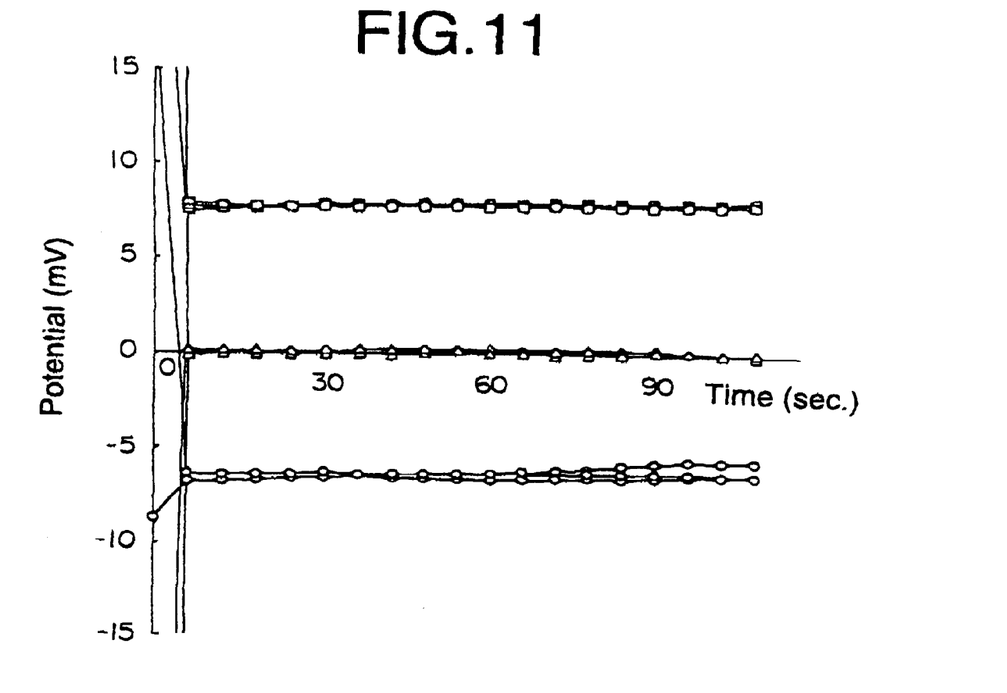
FIG. 11 graphically illustrates analytical performances of the chloride ion-detective electrode element of Example 5.

The results of measurements were graphically illustrated in FIG. 11, wherein the blank squares indicate the data measured using Standard Solution L as sample solution, the blank triangles indicate the data measured using Standard Solution M as sample solution, and the blank circles indicate the data measured using Standard Solution H as sample solution.

The results illustrated in FIG. 11 teach that a response in the measurement is quick and the measured value rapidly converges.

(2) Measurement of Electric Potential in the use of Potassium Ion-selective Electrode Element The measuring procedures of electric potential were repeated in the same manner as described above, for measuring potassium ion, using Standard Solutions L, M, and H, except for using the potassium ion-selective electrode element (which was prepared in Example 4) in place of the chloride ion-selective electrode element.

Figure 12:
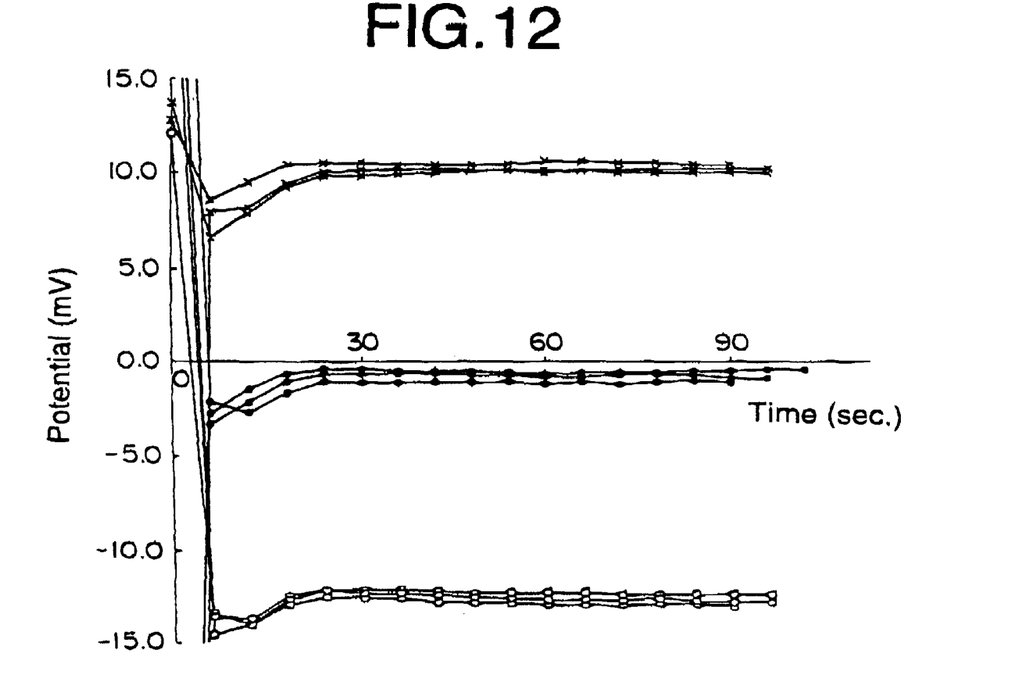
FIG. 12 graphically illustrates analytical performances of the potassium ion-detective electrode element of Example 5.

The results of the measurements are illustrated in FIG. 12, in which the cross marks, black circles and blank squares indicate, respectively, the measured values in the use of Standard Solutions L, M and H as the sample solutions. It is confirmed that a response in the measurement of potassium ion according to Nernst' equation is quick and the measured value rapidly converges.

(3) Measurement of Electric Potential in the use of Sodium Ion-selective Electrode Element The measuring procedures of electric potential were repeated in the same manner as described above, for measuring sodium ion, using Standard Solutions L, M, and H, except for using the sodium ion-selective electrode element (which was prepared in Example 4) in place of the chloride ion-selective electrode element.

Figure 13:
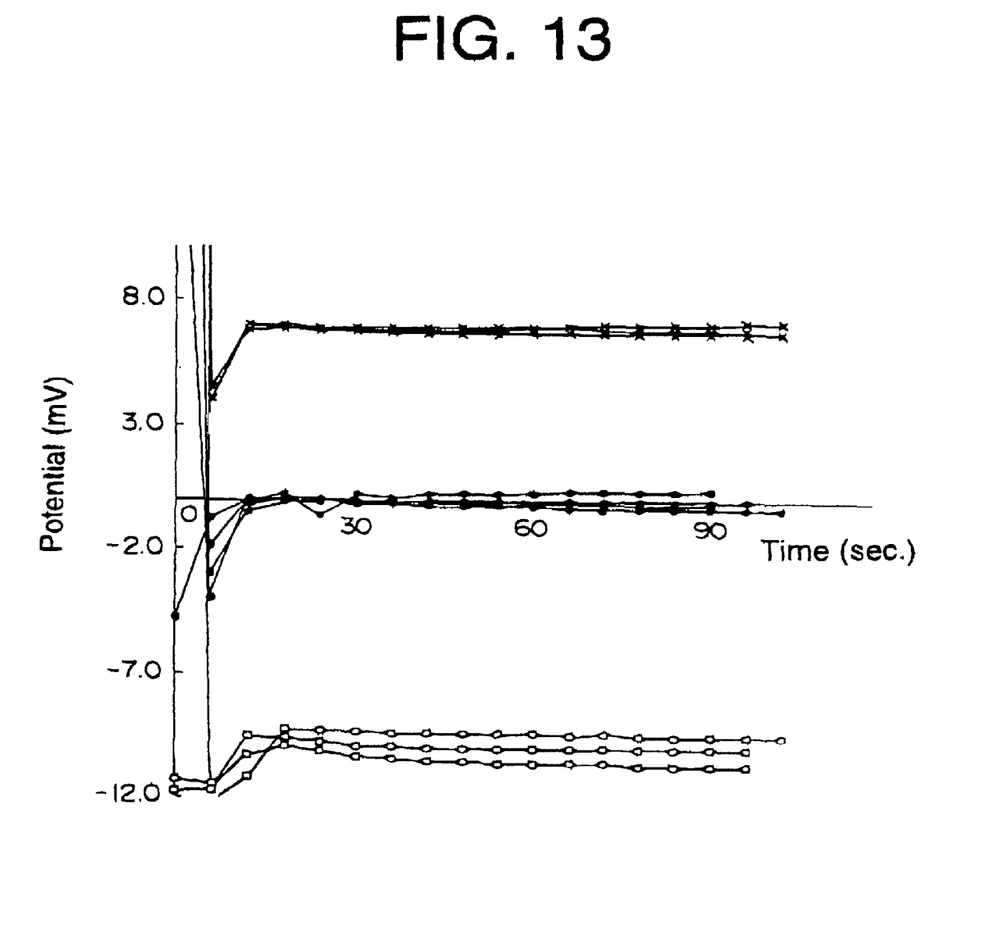
FIG. 13 graphically illustrates analytical performances of the sodium ion-detective electrode element of Example 5.

The results of the measurements are illustrated in FIG. 13, in the same manner as in FIG. 12. It is confirmed that a response in the measurement of sodium ion according to Nernst' equation is quick and the measured value rapidly converges.

EXAMPLE 6

The elemental analyses were performed on the silver/silver halide electrode prepared in Example 4, by means of a fluorescence X-ray meter (SEA 2001, available from Seiko Electronics Industry Co., Ltd.), to determine the amounts of several elements in the electrode. The results are set forth in Table 3, wherein the values are indicated in terms of strength (cps) of fluorescence X-rays.

TABLE 3

|  | Silver/Silver Halide Electrode | | |
| --- | --- | --- | --- |
|  | Example 4 | Com. Ex. 1 | Com. Ex. 2 |
| Chlorine | 121.71 | 140.93 | 121.33 |
| Chromium | 0.00 | 75.36 | 0.00 |
| Manganese | 0.00 | 0.00 | 52.09 |
| Iron | 4.56 | 0.00 | 0.00 |
| Silver | 292.09 | 288.94 | 291.28 |

It is confirmed that the silver/silver halide electrode prepared in Example 4 contains a small amount of iron. It is noted that contamination of such small amount of iron gives little adverse effect to the analytical performance of the ion-selective electrode element, as is shown in the data described hereinbefore.

EXAMPLE 7

A referential aqueous solution was prepared from 100 mM of sodium chloride, 30 mM of sodium hydrogen carbonate, 4 mM of potassium dihydrogen phosphate, 3 vol. % of PVPK-15, and 2 vol. % of glycerol. To the referential solution was added sodium bromide to give a solution containing the bromide ion of 4 mM, 6 mM, or 8 mM, to prepare a sample solution.

The referential solution was spotted simultaneously on the chloride ion-selective electrode element prepared in Example 5 in the referential solution-receiving area and the sample solution-receiving area. The chloride ion activity was measured at 60 sec., one week, two weeks, and four weeks, after the spotting.

In the same manner, the sample solution (bromide ion: 4 mM, 6 mM, 8 mM) was spotted in the sample solution-receiving area simultaneously with the referential solution (in the referential solution-receiving area), and the same measurements were carried out. The results of the measurements are illustrated in FIG. 14, in which the black rhombi, black squares, cross marks, and blank triangles indicate the values measured at 60 sec., one week, two weeks, and four weeks, respectively.

Figure 14:
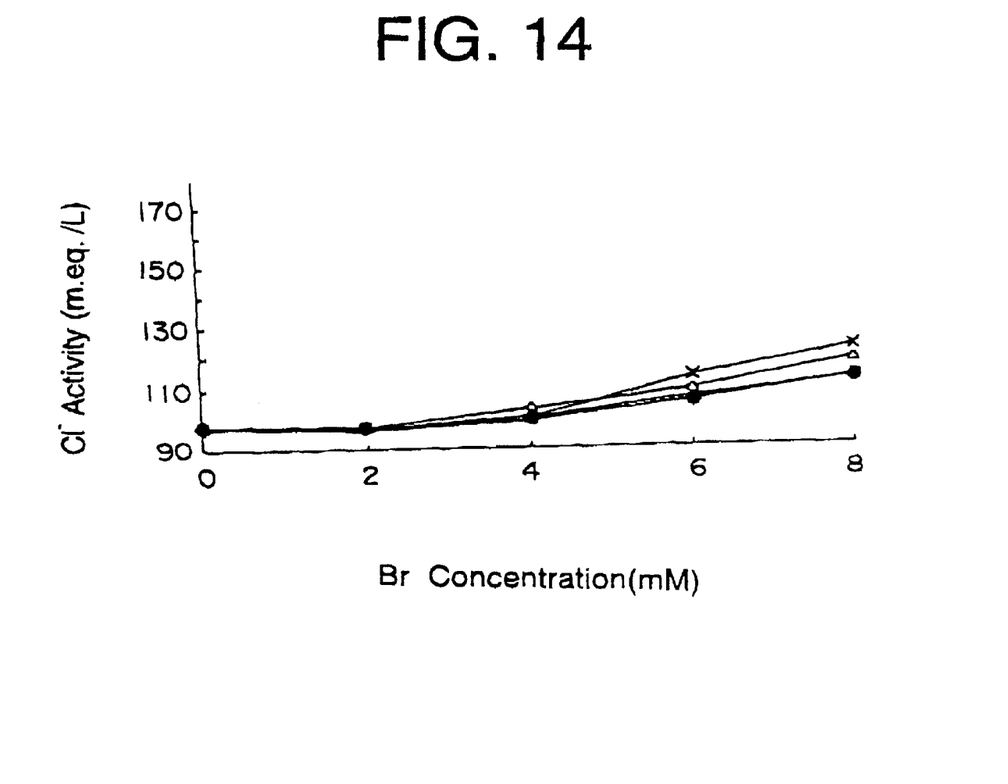
FIG. 14 graphically illustrates variations of a chloride ion activity measured in the presence of a bromide ion in different concentrations which were observed in the use of a chloride ion-selective electrode element of Example 7.

From the measured values illustrated in FIG. 14, the adverse effect to the measured chloride ion activity is kept small for a long period of time.

Comparison Example 3

The measurements of chloride ion activity of Example 7 were repeated except for employing the chloride ion-selective electrode element of Example 3 (in which the silver halide layer was prepared using potassium dichromate). The results of the measurements are illustrated in FIG. 15, in the same manner as in FIG. 14.

Figure 15:
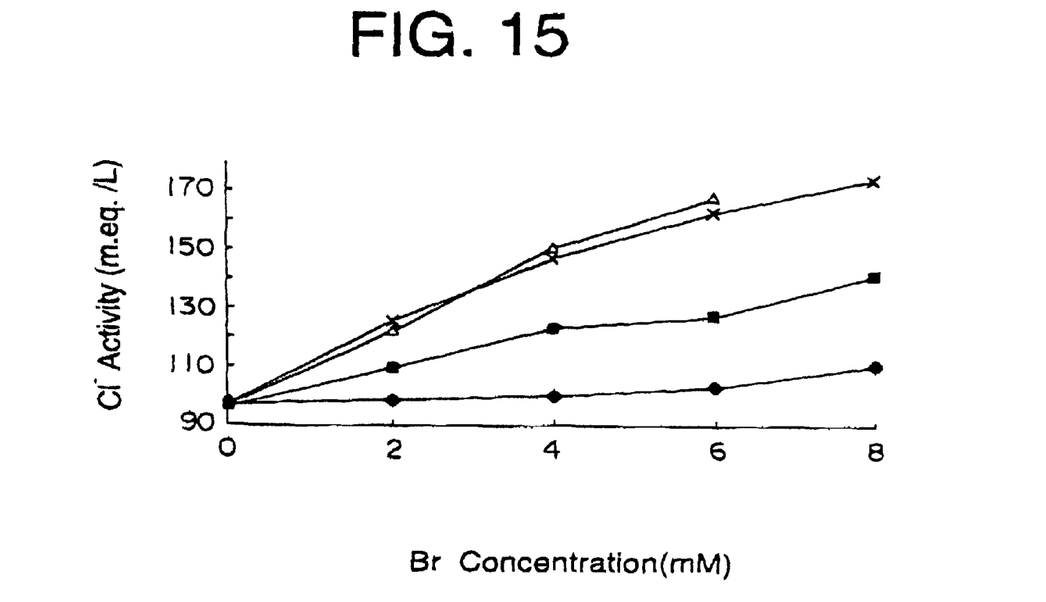
FIG. 15 graphically illustrates variations of a chloride ion activity measured in the presence of a bromide ion in different concentrations which were observed in the use of a chloride ion-selective electrode element of Comparison Example 2.

From the measured values illustrated in FIG. 15, the adverse effect to the measured chloride ion activity apparently increases when the spotted electrode is for a long period of time. This phenomenon is assumed to be caused by dichromate ion which was incorporated into the silver halide layer in the oxidizing procedure.

What is claimed is:

1. A method for producing an ion-selective silver/silver halide electrode element comprising a non-electroconductive support sheet, a silver metal layer, and a silver halide layer containing no heavy metal element, the method comprising oxidizing a silver metal layer provided on a non-electroconductive support sheet with an oxidizing compound which is selected from the group consisting of hydrogen peroxide, potassium peroxodisulfate and sodium peroxodisulfate, in the presence of a halide containing no heavy metal element.

2. The method of claim 1, wherein the oxidizing compound is hydrogen peroxide.

3. The method of claim 1, wherein the halide comprises ammonium halide, an alkali metal halide or an alkaline earth metal halide.

4. A method for producing an ion-selective silver-silver halide electrode element comprising a non-electroconductive support sheet, a silver metal layer, and a silver halide layer containing no heavy metal element, the method comprising oxidizing a silver metal layer provided on a non-electroconductive support sheet with a chelated ferric compound in the presence of a halide containing no heavy metal element.

5. The method of claim 4, wherein the chelated ferric compound is chelated with a compound selected from the group consisting of propanediamine tetraacetate, ethylenediamine tetraacetate, diethylenetriamine pentaacetate, triethylenetetramine hexaacetate, ethylenediamine disuccinate and tetrasodium N,N-dicarboxymethylgutamate.

6. The method of claim 4, wherein the halide comprises ammonium halide, an alkali metal or an alkaline earth metal halide.

* * * * *